(12) United States Patent
Nedwell

(10) Patent No.: US 9,422,743 B2
(45) Date of Patent: Aug. 23, 2016

(54) DECODING PIN LOCKS

(71) Applicant: Jeremy Nedwell, Bishop's Waltham Hampshire (GB)

(72) Inventor: Jeremy Nedwell, Bishop's Waltham Hampshire (GB)

(*) Notice: Subject to any disclaimer, the term of this patent is extended or adjusted under 35 U.S.C. 154(b) by 188 days.

(21) Appl. No.: 14/379,915

(22) PCT Filed: Feb. 15, 2013

(86) PCT No.: PCT/GB2013/050361
§ 371 (c)(1),
(2) Date: Aug. 20, 2014

(87) PCT Pub. No.: WO2013/124629
PCT Pub. Date: Aug. 29, 2013

(65) Prior Publication Data
US 2015/0033861 A1 Feb. 5, 2015

(30) Foreign Application Priority Data
Feb. 20, 2012 (GB) .................................. 1202819.7

(51) Int. Cl.
*E05B 19/20* (2006.01)
*G01N 29/12* (2006.01)
(Continued)

(52) U.S. Cl.
CPC ............. *E05B 19/205* (2013.01); *G01N 29/12* (2013.01); *G01N 29/348* (2013.01); *G01N 29/44* (2013.01)

(58) Field of Classification Search
CPC .................................................... E05B 19/205
USPC ........................................................ 33/540
See application file for complete search history.

(56) References Cited

U.S. PATENT DOCUMENTS

| 2,338,768 | A | * | 1/1944 | Johnstone | ............. | E05B 19/205 |
| | | | | | | 33/540 |
| 4,535,546 | A | * | 8/1985 | Smith | ................... | E05B 19/205 |
| | | | | | | 33/540 |
| 5,172,578 | A | * | 12/1992 | Bitzios | .................... | E05B 19/20 |
| | | | | | | 33/540 |

(Continued)

FOREIGN PATENT DOCUMENTS

| BR | WO 9820218 A1 * | 5/1998 | ........... E05B 19/205 |
| EP | 2025840 A1 | 2/2009 | |

OTHER PUBLICATIONS

International Search Report for PCT Application No. PCT/GB2013/050361, dated May 22, 2013, 3 pages.

(Continued)

*Primary Examiner* — Christopher Fulton
(74) *Attorney, Agent, or Firm* — Westman, Champlin & Koehler, P.A.

(57) ABSTRACT

In order to determine the particular cut possessed by a tumbler of a mechanical lock, the tumbler is stimulated with mechanical energy. The vibrational response of the tumbler is detected, and the detected response is used in determining which cut of the plurality of possible cuts the tumbler possesses. The cut of a lock tumbler is defined by its shape and/or size. For example, in the case of a pin-tumbler lock, the cut of a pin is defined by its length. Different cuts of tumbler will therefore exhibit different vibrational responses to stimulation by mechanical energy, and these different vibrational responses can be used to determine which cut the tumbler possesses, for example by comparing with the vibrational responses of real or modeled tumblers with known cuts. The response may be detected while the tumbler is being stimulated, and the responses to different frequencies of stimulation may be detected and processed.

18 Claims, 3 Drawing Sheets

(51) Int. Cl.
*G01N 29/34* (2006.01)
*G01N 29/44* (2006.01)

(56) References Cited

U.S. PATENT DOCUMENTS

| | | | | |
|---|---|---|---|---|
| 5,224,365 | A | * | 7/1993 | Dobbs .................. E05B 19/205 33/540 |
| 5,355,701 | A | * | 10/1994 | Tobias .................. E05B 19/205 70/352 |
| 6,722,172 | B2 | * | 4/2004 | Pinkhasov ............ E05B 19/205 33/540 |
| 7,243,437 | B1 | | 7/2007 | Estrada |
| 8,001,699 | B2 | * | 8/2011 | Randall ................. E05B 19/205 33/540 |
| 2003/0159480 | A1 | | 8/2003 | Pinkhasov et al. |
| 2011/0067254 | A1 | | 3/2011 | Randall |
| 2011/0071776 | A1 | * | 3/2011 | Andle .................. G01N 29/036 702/54 |
| 2015/0040413 | A1 | * | 2/2015 | Nedwell ............... E05B 19/205 33/540 |

OTHER PUBLICATIONS

Written Opinion of International Search Report for PCT Application No. PCT/GB2013/050361, dated May 22, 2013, 6 pages.

* cited by examiner

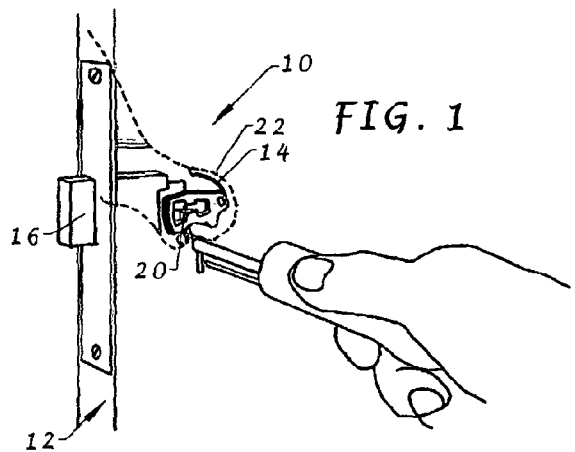
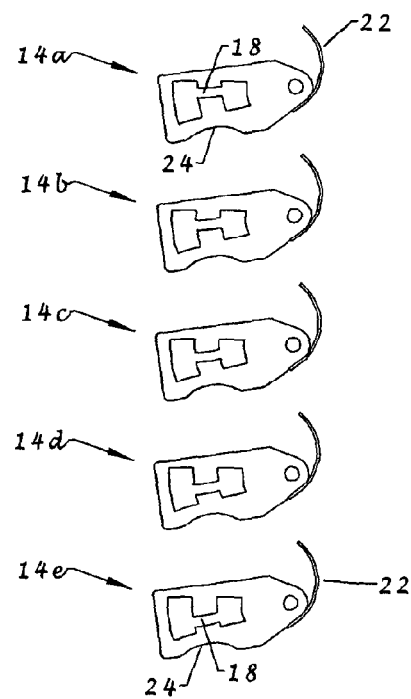
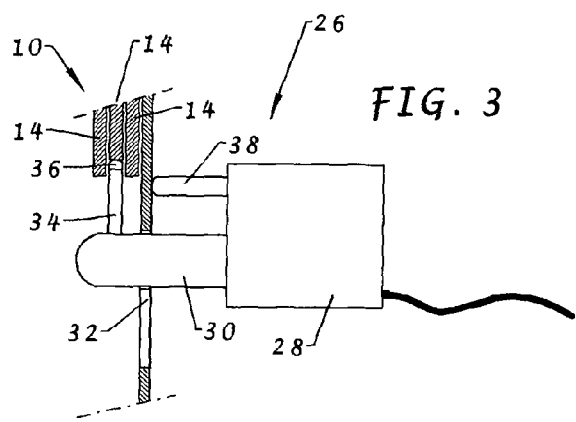

DECODING PIN LOCKS

CROSS-REFERENCE TO RELATED APPLICATION

This Application is a Section 371 National Stage Application of International Application No. PCT/ GB2013/ 050361, filed 15 Feb. 2013 and published as WO 2013/ 124629 A1 on 29 Aug. 2013, in English, the contents of which are hereby incorporated by reference in their entirety.

This invention relates to a method, apparatus and transducer for use in determining the cut of a mechanical lock or of a tumbler in a mechanical lock.

The invention is applicable to a mechanical lock which is arranged to be unlocked by a key. In order to do this, first the key must be of a design which can be inserted into the lock. Second the key must have the correct 'cut' so that when fully inserted into the lock it moves at least one tumbler (but usually between three and nine tumblers) in the lock each to a position in which the lock can be released. Each tumbler has one of several possible cuts, typically between three and ten cuts. The combination of the particular cuts of the tumblers and the order in which they are arranged in the lock defines the cut of the lock, and the cut of the key needs to complement the cut of the lock in order that the key will work. Locks are usually designed so that it is not possible to read the cut of the lock by external visual inspection.

There are occasions when a lock needs to be lawfully unlocked but none of the keys for that lock is available, for example because they have all been lost. In this case, an attempt may be made by a skilled locksmith to pick the lock. If successful, the lock can then usually be replaced, or the lock can be disassembled so that its cut can be determined and the lock can be re-keyed. However, some locks are extremely difficult, or impossible, to pick. If a complete range of possible keys for a lock is available, each of them may be tried in the lock in turn until a key that works is found. However, the number of possible cuts of key for a particular design of lock may be very high, of the order of ten thousand, a hundred thousand, a million or more, and so in most cases this is an impracticable method. As a last resort, it may be necessary to break the lock or the structure to which it is fitted.

An aim of the invention, or least of specific embodiments of it, is to enable the cut of a locked lock to be determined without the need to pick the lock and without the need for dismantling the lock so that, for example, a key with a complementary cut can be manufactured and the lock can be unlocked.

The invention is applicable to many different types of lock, including pin-, wafer-, disc- and lever-tumbler locks.

In accordance with a first aspect of the present invention, there is provided a method of determining a particular cut possessed by a tumbler of a mechanical lock, the particular cut being one of a plurality of possible cuts. The method comprises the steps of: stimulating the tumbler with mechanical energy; detecting the vibrational response of the tumbler to the stimulation; and processing the detected response in determining which cut of the plurality of possible cuts the tumbler possesses.

The cut of a tumbler is defined by its shape and/or size. For example, in the case of a pin-tumbler lock, the cut of a pin is defined by its length. Different cuts of tumbler will therefore exhibit different vibrational responses to stimulation by mechanical energy, and these different vibrational responses can be used to determine which cut the tumbler possesses, for example by comparing with the vibrational responses of real or modelled tumblers with known cuts.

In a preferred embodiment of the invention, the response is detected while the tumbler is being stimulated.

Preferably, the tumbler is stimulated at at least two frequencies so that the tumbler vibrates, and the response of the tumbler to vibration at each of the stimulation frequencies is detected. For example, the tumbler may be stimulated at at least two (and preferably many) discrete stimulation frequencies in succession. Alternatively, the tumbler may be stimulated at a stimulation frequency which is swept substantially continuously between two values. In another variant, the tumbler may be stimulated at at least two (and preferably many) different stimulation frequencies simultaneously, for example with white noise.

In one example, the method includes the steps of: storing, for each possible cut, at least one reference resonant frequency value for that cut; determining at which of the stimulation frequencies a resonance peak is produced in the response of the tumbler with the particular cut; and determining which particular cut the tumbler possesses by comparing the resonance peak frequency or frequencies with the reference frequency or frequencies. This technique is useful where the tumbler design is such that it has a particular resonance at a frequency which changes in an ordered way as the cut is changed in an ordered way.

In another example, the method includes the steps of: storing, for each possible cut, at least one reference frequency-domain response spectrum for that cut; producing from the detected responses a detected frequency-domain response spectrum for the tumbler; and comparing the detected spectrum with the reference spectra. In this case, each comparing step may use an algorithm which produces a quality-of-match value dependent on the quality of match between the detected spectrum and the respective reference spectrum; and the cut of the tumbler may be determined from which reference spectrum produces the best quality-of-match value. The quality-of-match value for each reference spectrum is preferably weighted in favour of peaks in the detected spectrum which match peaks in that reference spectrum. The quality-of-match value for each reference spectrum is also preferably weighted against peaks in the detected spectrum which do not match peaks in that reference spectrum and/or against peaks in that reference spectrum which do not match peaks in the detected spectrum. Each of the reference spectra is preferably normalised, and the method may further comprise the step of normalising the detected spectrum prior to comparison with the stored spectra.

Resonances (or the characteristic response of a tumbler) may also be detected by means not involving a spectrum. For instance, Prony analysis may be used to model a time history response of the tumbler as being due to a limited set of damped sinusoidal transients, which will have frequencies similar to the resonant frequencies of the preceding example. These transients may equally be used as a means of identifying tumblers.

The stimulating step preferably comprises: providing a driving transducer which moves in response to an electrical driving signal; driving the driving transducer with an electrical signal; and transmitting the resultant movement of the driving transducer to the tumbler.

The detecting step preferably comprises: providing a detecting transducer which generates an electrical detection signal in response to movement of the detecting transducer; and transmitting the vibrational response of the tumbler to the detecting transducer.

The driving transducer and the detecting transducer may be separate devices. However, a common transducer may conveniently serve as the driving transducer and as the detecting transducer. For example, in the case where a piezoelectric transducer is driven with a voltage signal, the vibration of the tumbler causes a back EMF in the transducer which affects the current flowing in the transducer, and the change in current so caused can be detected.

The root mean square level of the detection signal is preferably used, and in the case of a continuous frequency spectrum the root mean square signal may be smoothed over a narrow frequency band.

The invention extends, in a second aspect thereof, to a method of determining a cut of a mechanical lock having a plurality of tumblers each possessing one of a plurality of possible cuts. The method comprises the steps of performing the method of the first aspect of the invention on each of the tumblers. For a design of lock which is known other than its cut, once the cut of each of its tumblers has been determined, the cut of the lock as a whole and therefore of the required key can be determined.

A third aspect of the invention provides a transducer assembly for use in determining a particular cut possessed by a tumbler of a mechanical lock. The transducer assembly comprises: a shaft or blade for insertion into a keyhole of the lock; and at least one transducer mounted on the shaft or blade and arranged to vibrate the tumbler and to detect vibration of the tumbler. The transducer assembly may additionally include a gauge for gauging the depth to which the shaft or blade is inserted into the lock. When used with a lock having a plurality of tumblers, the shaft or blade can therefore be moved to align the tumblers one after another. Alternatively, a plurality of such transducers may be provided arranged along the shaft or blade, and a register may be provided for engaging the lock and registering the transducer assembly with respect to the lock in the longitudinal direction of the shaft or blade.

In accordance with a fourth aspect of the invention, there is provided an apparatus for determining a cut of a tumbler of a mechanical lock. The apparatus comprises means for performing at least the stimulating step and the detecting step as defined for the method of the first aspect of the invention. At least part of the processing step of the method may be performed by a human operator. However, the apparatus may further comprise a means for performing the processing step at least in part automatically. The apparatus preferably employs a transducer assembly according to the third aspect of the invention.

A specific embodiment of the present invention will now be described, purely by way of example, with reference to the accompanying drawings, in which:

FIG. 1 is a partly cut away view of a lever tumbler lock fitted to a door and a first embodiment of transducer assembly;

FIG. 2 shows a set of five possible cuts of lever tumbler which may be used in such a lock;

FIG. 3 is a schematic sectioned view through the lock and showing the transducer assembly;

Figure 4:
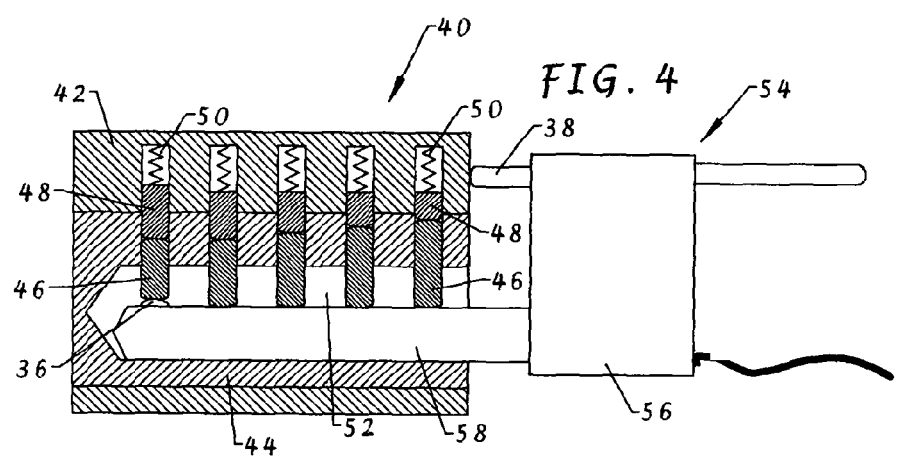
FIG. 4 is a schematic sectioned view of a pin tumbler lock and a second embodiment of transducer assembly.

Referring to FIGS. 1 and 2, a lever tumbler lock 10 fitted to a door 12 has a set of three lever tumblers 14 which normally prevent a bolt 16 from moving. However, each tumbler 14 has a gateway 18 through which a projection 20 from the bolt 16 can pass if the tumbler 14 is raised, against the action of a leaf spring 22, a particular amount by a key bearing against the lower edge 24 of the tumbler 14. Each tumbler 14 is identical to one of a set of five tumblers 14a-e as shown in FIG. 2. The tumblers 14a-e are identical except that each has its gateway 18 at a different angular position. The tumblers 14a-e therefore need to be raised by differing amounts by the key in order to bring their gateways 18 horizontal so that the projection 20 on the bolt 16 can pass though them. This is what gives each of the tumblers 14a-e its different cut.

The invention utilises the effect that if each lever tumbler 14 of the lock 10 is stimulated mechanically at a position along its lower edge 24 that is accessible through the keyhole, then the tumbler 14 will respond differently in dependence upon which of the five cuts the tumbler 14 possesses. By detecting the response and comparing the response to predetermined reference responses for each of the five cuts of tumbler 14, it is possible to determine which cut that tumbler 14 possesses. Once the cuts of all of the tumblers 14 have been determined and the order of them, then if the model of lock is known, it is possible to manufacture a key that will fit the lock.

FIG. 3 shows a transducer assembly 26 for stimulating the tumblers 14 in turn. The assembly 26 comprises a body 28, a shaft 30 projecting from the body 28 so that it can be inserted through the keyhole 32 into the lock 10, and an arm 34 mounted on the shaft 30 so that it too can be inserted through the keyhole 32. The arm 34 radiates from the shaft 30 and has a transducer device 36 mounted at its tip so that when the shaft 30 is turned, for example through half a turn, the transducer device 36 can engage the lower edge 24 of one of the tumblers 14, depending on how far the shaft 30 has been inserted into the lock 10. To assist in setting or measuring the insertion distance, a depth gauge 38 is provided on the body 28.

Referring to FIG. 4, a different type of lock, namely a pin tumbler lock 40, is schematically shown having a body 42 and a cylindrical plug 44 fitted in the body 42. Five pairs of abutting pins 46,48 are a sliding fit in aligned holes in the body 42 and plug 44, and the pins 46,48 are urged inwards by springs 50 so that the inner tumbler pins 46 project into a keyway 52 and so that the outer driver pins 48 rest partly in the body 42 and partly in the plug 44. Although the total length of each pair of pins 46,48 is typically identical, the tumbler pins 46 can be of different lengths, as too can the driver pins 48. It is the length of each tumbler pin 46 that defines its cut. In the example shown, there are five different cuts of the tumbler pins 46. When a key (not shown) is fully inserted into the keyway 52 it raises each pair of pins 46,48 by individual amounts according to the cut of the key. If the keys fits, then the shear line between each tumbler pin 46 and its driver pin 48 will line up with the shear line between the outer surface of the plug 44 and the body 42, so that the plug 44 can then be turned in the body and operate an unlocking mechanism.

Again, the invention utilises the effect that if each tumbler pin 46 of the lock 40 is stimulated mechanically at its lower end that is accessible through the keyway 52, then the tumbler pin 46 will respond differently in dependence upon which of the five cuts the tumbler pin 46 possesses. By detecting the response and comparing the response to predetermined reference responses for each of the five cuts of tumbler pin 46, it is possible to determine which cut that tumbler pin 46 possesses. Once the cuts of all of the tumbler pins 46 have been determined and the order of them, then if the model of lock is known, it is possible to manufacture a key that will fit the lock.

FIG. 4 also shows a transducer assembly 54 for stimulating the tumbler pins 46 in turn. The assembly 54 comprises a body 56 and a blade 58 projecting from the body 56 so that it can be inserted into the keyway 52. A transducer device 36 is mounted on the blade 58 so that it can engage the lower end of any one of the tumbler pins 46, depending on how far the blade 58 has been inserted into the lock 40. To assist in setting or measuring the insertion distance, a depth gauge 38 is provided on the body 56.

Figure 5:
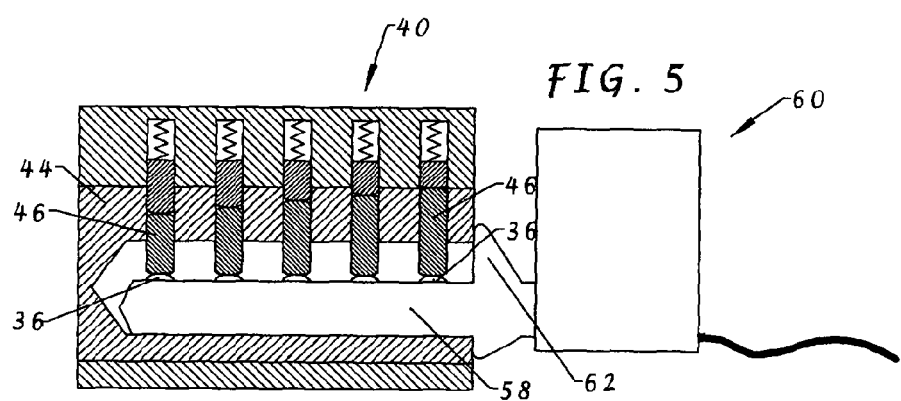
FIG. 5 is similar to FIG. 4, but showing a third embodiment of transducer assembly.

FIG. 5 shows an alternative transducer assembly 60 for stimulating the tumbler pins 46 of the lock of FIG. 4. In this case, a separate transducer device 36 is provided for each tumbler pin 46. A depth gauge 38 is therefore unnecessary, but the blade 58 is formed with a fixed register 62 which engages the end of the plug 44 of the lock 40 when the blade 58 is in its proper position.

The transducer device 36 used in the transducer assemblies 26,54,60 of FIGS. 3 to 5 may comprise an element 64 of a piezoelectric material, a magnetostrictive material, or another material which changes shape when a voltage or other signal is applied to it.

Figure 6:
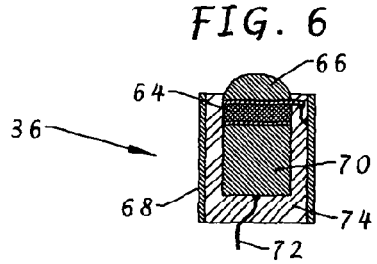
FIG. 6 is a schematic sectioned view of one arrangement of transducers that may be used in the transducer assemblies.

One design of transducer device 36 is shown in FIG. 6. In the simplest case, the element 64 is placed in contact with the tumbler 14,46, so that the vibration of the element 64 may be transferred to the tumbler 14,46 and vice versa. However, since this may cause wear of the element 64, and also to improve the transmission of energy, the vibration may be transferred between the element 64 and the tumbler 14,46 through a thin layer of compliant material and/or an anvil 66, or hard structure, attached to the outer face of the element 64, which is designed to couple movement efficiently between the transducer element 64 and the tumbler 14,46. As shown in FIG. 6, the device 36 has an electrically conductive tubular sleeve 68 to which a 'ground' electrode of the element 64 is bonded, and an electrically conductive backing mass 70 which is bonded to the 'signal' electrode of the element 64 and also provides a connection for a signal cable 72. The element 64 and backing mass 70 are potted in the sleeve 68 by a non-conductive material 74 such as plastic or rubber which may additionally serve to insulate the element 64 from the shaft 30 or blade 58 of the transducer assembly 26,54,60.

Figure 7:
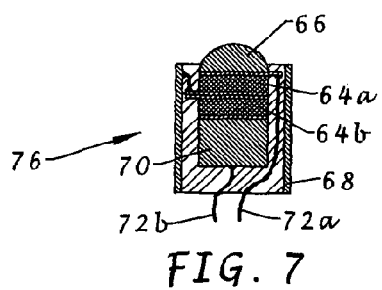
FIG. 7 is a schematic sectioned view of another arrangement of transducer that may be used in the transducer assemblies.

Another design of the transducer device 76 is shown in FIG. 7. In this case, there are two transducer elements 64a,b, namely a receiving transducer element 64a immediately underneath the anvil 66, and a transmitting transducer element 64b sandwiched between the receiving element 64a and the backing mass 70. The abutting electrodes of the elements 64a,b are electrically bonded to the ground sleeve 68, and separate receiving and transmitting signal cables 72a,b are electrically connected to the other electrode of the receiving element 64a and to the backing mass 70.

Figure 8:
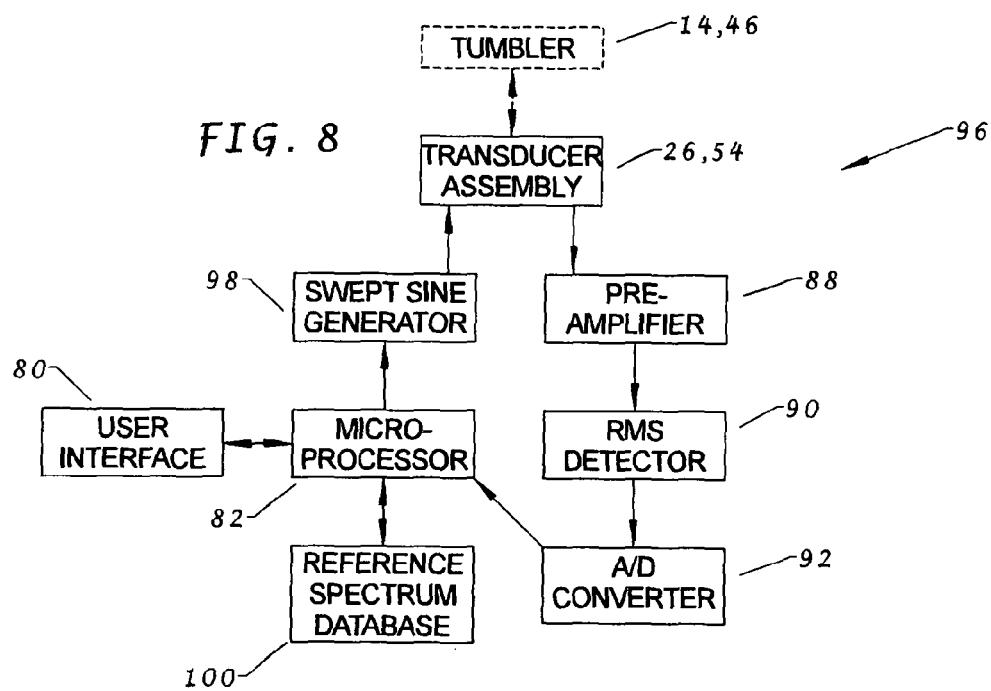
FIG. 8 is a block diagram of a lock cut determining apparatus according to the invention.

An apparatus 96 for use in determining the cut of the lock 10,40 using a transducer assembly 26,54 with a transducer device 76 is shown schematically in FIG. 8. In response to a command from a user interface 80, a microprocessor 82 is programmed to trigger a swept sine generator 98 to commence a sweep. In response, the generator 98 produces a constant amplitude sinusoidal electrical output signal having a frequency which progressively varies from one limit to another, for example between 20 kHz and 250 kHz, in a predetermined manner. For example, the sweep rate (i.e. the change in frequency per unit time) may be constant. Alternatively, the frequency may be swept logarithmically such that the frequency doubles in equal increments of time. The output of the generator 98 is fed to the transmitting transducer element 64b of a transducer device 76 (as described with reference to FIG. 7) in the transducer assembly 26,54. As a result, the tumbler 14,46 in contact with the transducer device 36 vibrates. The receiving transducer element 64a in the transducer device 76 produces a voltage signal related to the amount of vibration of the tumbler 14,46 and is connected to the input of a preamplifier 88 which amplifies the voltage signal that it receives and passes it to a root-mean-square detector circuit 90. The circuit 90 produces as an output a voltage signal which is the RMS level of the input signal, optionally smoothed over a short period of time. This RMS signal is then converted to a digital signal by an A to D converter 92, and a stream of samples of the digital signal are input to the microprocessor 82. The microprocessor 82 is then programmed to perform any of a number of operations on the received data stream, such as storing it, representing it in graphical form to the user interface 80, and/or processing it and data in a reference spectrum database 100 so as to determine which cut is possessed by the tumbler 14,46 under test, as will be described in more detail below. The above process is then repeated for each of the other tumblers 14,46 in the lock 10,40.

If the level of the returning signal is recorded as a function of time, and since the signal is swept at a known rate over frequency, the level of the returning signal may be presented as a function of frequency. The function describing the level of the returning signal as a function of the frequency at which the tumbler 14,46 is being driven may be considered to be an estimate of the frequency-domain spectrum of the locking mechanism's response. As the frequency of the driving signal changes, there will be specific frequencies at which the locking mechanism resonates or is easier to drive. At these frequencies, the received signal will vary in level from the level at other frequencies. It is these variations in the behaviour of the locking mechanism that may be used to determine its cut.

If the frequency range is well chosen and wide enough, the characteristic of the tumbler 14,46 will contain many resonances and changes in vibration level that depend only on the structure of the tumbler 14,46 with which the transducer assembly is in contact. By comparing these with the measured resonant behaviour of tumblers having a known cut, or the estimated resonant behaviour calculated using a suitable model, such as a finite element modelling, it is possible to determine the structure within the lock and hence determine its cut.

Figure 9:
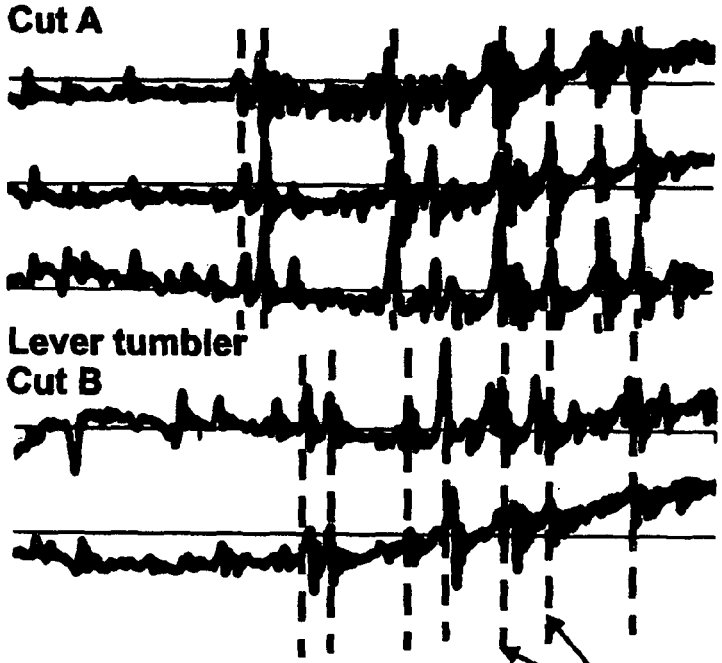
FIG. 9 shows sample signal spectra that may be acquired by the apparatus.

FIG. 9 shows the outputs of the A to D converter 92 as a function of frequency of five tumblers 14 of a commercially available lever tumbler lock. The upper three traces (or frequency-domain response spectra) are for tumblers 14 of one cut, and the lower two spectra are for another cut. As can be seen, the spectra for tumblers which have the same cut are very similar. However, the spectra for tumblers having different cuts are dissimilar. Hence, where a reference set of frequency-domain response spectra have been acquired for a particular lock type and all permissible cuts, having at least one example of each cut but preferably many, it is possible to determine the cut of an unknown lock by comparing the frequency-domain response spectra of the unknown tumblers within it to the reference set of spectra. By finding the cut of each tumbler that matches most closely to the known reference cuts, the cut of that tumbler may be determined.

In the simplest case, a trained operator of the apparatus 78 might simply recognise the response spectrum of a cut from previous experience. However, it is preferable to aid the operator in recognising the cut by visually comparing the response spectrum of the unknown cut against each reference spectrum. For instance, the reference and unknown spectra may be overlaid on the same graph, to determine whether the peaks, troughs, and other features of the reference and unknown spectra are similar These features may be used by the operator to visually determine which reference cut matches the unknown cut best.

Alternatively, it is possible for the microprocessor 82 to use a suitable algorithm to compare the spectrum for the unknown pin and the reference spectra automatically. For instance, the unknown spectrum may be correlated against each of the reference spectra, to find the reference spectrum that provides the best match.

It should be noted that where the reference spectra have dissimilar levels, for instance if the contact between the transducer and the tumbler was better in one case than another when the signal was acquired, a matching algorithm may tend to favour a pulse having the highest level. Therefore, in order to compare the unknown spectrum more accurately and select those that offer the best matches, it is beneficial to normalise at least the reference spectra first, in order to bring the average amplitude of them all to the same level. For instance, in producing a normalised reference spectrum, the RMS signal output from the A to D converter 92 can be normalised by dividing it by the overall root mean square level of the entire time history for that spectrum. In other words, if a digital unnormalised reference spectrum is made up of N data points having values U(i) for I=1 to N, then the corresponding N data points having values R(i) in the normalised spectrum can be calculated as:

$$R(i) = \frac{U(i)}{\sum_{j=1}^{j=N} U(j)}$$

One suitable algorithm to find the quality of match Q between the N-point root mean square frequency-domain response spectrum X(i) for an unknown tumbler and a normalised reference spectrum R(i) is given by:

$$Q = \sum_{i=1}^{i=N} X(i) \cdot R(i)$$

Thus, the microprocessor 82 multiplies each i-th point in the unknown spectrum by the corresponding point in the reference spectrum, and sums the values over all N point pairs. It will be appreciated that where peaks in both the reference and unknown frequency-domain spectra coincide, a high value will be multiplied by a high value and its addition to the quantity Q will be high, thus making it to tend to a large value. Where the peaks do not coincide, Q will be correspondingly low as in general a high value will be multiplied by a low value at each point. Thus, if the quantity Q is calculated using the unknown spectrum and for all of the reference spectra, it may be used to select the best match by determining the reference spectrum that yields the highest value of Q.

It may be noted that whereas this algorithm provides a high value for peaks that coincide, it does not provide a penalty when a peak occurs in the reference spectrum that does not exist in the unknown spectrum, and vice-versa. It may therefore be beneficial to use an algorithm which ensures that the match is the best possible, by not only ensuring that peaks in the unknown spectrum coincide with peaks in the reference spectrum, but also that no peaks exist in the unknown spectrum that are not matched by peaks in the reference spectrum and vice-versa. For instance, the degree of existence $W_1$ of unmatched peaks in the unknown spectrum when compared with the reference may be estimated by:

$$W_1 = \sum_{i=1}^{i=N} \frac{X(i)}{R(i)}$$

Similarly, the degree of existence $W_2$ of unmatched peaks in the reference spectrum when compared with the unknown spectrum is given by:

$$W_2 = \sum_{i=1}^{i=N} \frac{R(i)}{X(i)}$$

Thus, a corrected value of the quality of match Q' that penalises for unmatched peaks is given by $$Q' = A.Q - B.W_1 - C.W_2$$

where A, B and C are constants determined by experiment to give the best match.

Various modifications and developments may be made to the embodiments of the invention described above.

For example, it will be appreciated that the matching algorithms are provided by means of example, and there are many other algorithms which might be used to match the detected and reference spectra. The use of analysis systems such as neural networks may provide better matching.

Also, it has been found that the level of a resonant peak may be affected by the exact point at which the transducer touches. This is because it is easier to drive a resonance at the point at which the displacement caused by the resonance is greatest; if the point at which the transducer touches is a null for the resonance, in which no movement occurs since the bending occurs around that point, it will not be driven at all. However, since the resonances are characteristic of the mechanical structure of the tumbler, the existence of the peak and the frequency at which it occurs is of more significance than its level. Thus an algorithm that detects and compares where the various peaks of the resonant frequency occur in the known and unknown characteristic spectra, rather than their level, may be best for identifying the cut of the unknown tumbler. For instance, it may be possible to tabulate several resonant frequencies of each of the cuts. By finding the best agreement, say within a narrow range of frequency that is sufficient to allow for manufacturing variations, between the resonant frequencies of the unknown tumbler, and the tabulated frequencies of the known cuts, it would be possible to determine which the unknown cut is.

An alternative method is to focus on one particular resonant frequency of the characteristic spectrum that is easily excited, and characteristic of the particular tumbler. For instance, it is commonly the case that a notch or "gate" on the lever mechanism changes its position. This causes the rotational inertia of the locking mechanism to change. Hence, it is possible to find resonant frequencies that move slightly upwards or downwards as the cut of the lock varies.

Thus, this particular resonant frequency of the unknown locking mechanism indicates which cut it is. In addition, even where the exact cut is unknown, scrutiny of the resonant frequencies may indicate whether one cut is higher or lower than those adjacent to it. This information may be of value to a locksmith in determining the cut of the lock even when it is of an unknown type.

An alternative but equivalent way of determining the way in which the vibration of the tumbler changes as a function of frequency may be provided by driving the transmitting transducer with any arbitrary signal, such as, for instance, white noise, and recording the response of the receiving transducer. Both the voltage waveforms of the driving signal and the received signal may be converted into a digital form by using suitable analogue-to-digital conversion electronics. Once the waveforms have been converted into a digital form, their equivalent frequency components may be estimated by use of a suitable processing algorithm such as the digital Fourier transform, which provides as an output the frequency spectrum of the electrical signal. Division of the transform of the received response by the transform of the transmitted signal yields a quantity that is similar to the spectrum of the preceding example, and which also indicates the spectrum of the vibrational behaviour of the locking mechanism.

In the apparatus 78 of FIG. 8, instead of using a transducer device 76 (FIG. 7) in the assembly 26,54, a transducer device 36 (FIG. 6) may be employed with its single transducer element 64 connected to the output of the swept sine generator 98. In this case, the input to the preamplifier 88 may be derived from a current sensing circuit which senses the current supply to the transducer assembly 26,54. The vibration of the tumbler causes a back EMF in the transducer element 64, which may serve to increase or decrease the current flowing through the transducer. The change in current may be measured, and hence the vibration of the locking mechanism inferred.

It should be noted that the embodiment of the invention has been described above purely by way of example and that many modifications and developments may be made thereto within the scope of the present invention.

The invention claimed is:

1. A method of determining a particular cut possessed by a tumbler of a mechanical lock, the particular cut being one of a plurality of possible cuts, the method comprising the steps of:
   stimulating the tumbler with at least two frequencies of mechanical energy so that the tumbler vibrates;
   detecting the vibrational response of the tumbler to each of the stimulation frequencies; and
   processing the detected response in determining which cut of the plurality of possible cuts the tumbler possesses.

2. A method as claimed in claim 1, wherein:
the response is detected while the tumbler is being stimulated.

3. A method as claimed in claim 1, wherein:
the tumbler is stimulated at least two discrete stimulation frequencies in succession.

4. A method as claimed in claim 1, wherein:
the tumbler is stimulated at a stimulation frequency which is swept substantially continuously between two values.

5. A method as claimed in claim 1, wherein:
the tumbler is stimulated at least two different stimulation frequencies simultaneously.

6. A method as claimed in claim 5, wherein:
the tumbler is stimulated with white noise.

7. A method as claimed in claim 1, and including the steps of:
   storing, for each possible cut, at least, one reference resonant frequency value for that cut;
   determining at which of the stimulation frequencies a resonance peak is produced in the response of the tumbler with the particular cut; and
   determining which particular cut the tumbler possesses by comparing the resonance peak frequency/ies with the reference frequencies.

8. A method as claimed in claim 1, and including the steps of:
   storing, for each possible cut, at least one reference frequency-domain response spectrum for that cut;
   producing from the detected responses a detected frequency-domain response spectrum for the tumbler; and
   comprising the detected spectrum with the reference spectra.

9. A method as claimed in claim 8, wherein:
each comparing step uses an algorithm which produces a quality-of-match value dependent on the quality of match between the detected spectrum and the respective reference spectrum; and
the cut of the tumbler is determined from one or more reference spectra producing the best quality-of-match value.

10. A method as claimed in claim 9, wherein:
the quality-of-match value for each reference spectrum is weighted in favor of peaks in the detected spectrum which match peaks in that reference spectrum.

11. A method as claimed in claim 9, wherein:
the quality-of-match value for each reference spectrum is weighted against peaks in the detected spectrum which do not match peaks in that reference spectrum and/or against peaks in that reference spectrum which do not match peaks in the detected spectrum.

12. A method as claimed in claim 8, wherein:
each of the reference spectra is normalized.

13. A method as claimed in claim 8, further comprising the step of:
normalizing the detected spectrum prior to comparison with the stored spectra.

14. A method as claimed in claim 8, wherein:
the stimulating step comprises:
   providing a driving transducer which moves in response to an electrical driving signal;
   driving the driving transducer with an electrical signal; and
   transmitting the resultant movement of the driving transducer to the tumbler.

15. A method as claimed in claim 14, wherein:
the detecting step comprises:
   providing a detecting transducer which generates an electrical detection signal in response to movement of the detecting transducer; and
   transmitting the vibrational response of the tumbler to the detecting transducer.

16. A method as claimed in claim 15, wherein:
a common transducer serves as the driving transducer and as the detecting transducer.

17. A method as claimed in claim 15, wherein:
a root mean square level of the detection signal.

18. A method as claimed in claim 15, wherein:
a smoothed root mean square level of the detection signal is used.

* * * * *